(12) United States Patent  (10) Patent No.: US 7,728,966 B2
Kim et al.  (45) Date of Patent: Jun. 1, 2010

(54) OPTICAL INSPECTION TOOL HAVING LENS UNIT WITH MULTIPLE BEAM PATHS FOR DETECTING SURFACE DEFECTS OF A SUBSTRATE AND METHODS OF USING SAME

(75) Inventors: Jong-An Kim, Seoul (KR); Dong-Chun Lee, Gyeonggi-do (KR); Chung-Sam Jun, Gyeonggi-do (KR); Ik-Chul Kim, Gyeonggi-do (KR); Sang-Hee Kim, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 332 days.

(21) Appl. No.: 11/423,677

(22) Filed: Jun. 12, 2006

(65) Prior Publication Data

US 2007/0013901 A1  Jan. 18, 2007

(30) Foreign Application Priority Data

Jul. 18, 2005  (KR) ..................... 10-2005-0064971

(51) Int. Cl.
  *G01N 21/00* (2006.01)
(52) U.S. Cl. .............. 356/237.2; 356/237.1; 356/237.3
(58) Field of Classification Search ... 356/237.1–237.6, 356/239.7–239.8, 241.3
  See application file for complete search history.

(56) References Cited

U.S. PATENT DOCUMENTS

| 4,679,937 | A | * | 7/1987 | Cain et al. ................... 356/138 |
| 5,428,442 | A | * | 6/1995 | Lin et al. .................. 356/237.5 |
| 5,631,733 | A | | 5/1997 | Henley |
| 5,909,276 | A | | 6/1999 | Kinney et al. |
| 2002/0180959 | A1 | * | 12/2002 | Nakajima et al. ........ 356/237.1 |

FOREIGN PATENT DOCUMENTS

JP  09-033446  2/1997
JP  08-233747  9/1999

OTHER PUBLICATIONS

English language abstract of Japanese Publication No. 08-233747.
English language abstract of Japanese Publication No. 09-033446.

* cited by examiner

*Primary Examiner*—Gregory J Toatley, Jr.
*Assistant Examiner*—Tri T Ton
(74) *Attorney, Agent, or Firm*—Volentine & Whitt, PLLC

(57) ABSTRACT

An optical inspection tool used to detect surface defects of a substrate include a chuck for holding a substrate and a lens unit disposed over the chuck. The lens unit includes at least a pair of oblique beam paths therein, wherein light penetrating the beam paths travels without angular deflection. The beam paths take the form of spaces formed through the lens unit, or flat portions formed on a lens within the lens unit. A camera is installed on the lens unit, and the camera converts light passing through the lens unit into an image. Methods of detecting surface defects of the substrate using the inspection tool are also provided.

31 Claims, 11 Drawing Sheets

OPTICAL INSPECTION TOOL HAVING LENS UNIT WITH MULTIPLE BEAM PATHS FOR DETECTING SURFACE DEFECTS OF A SUBSTRATE AND METHODS OF USING SAME

CROSS-REFERENCE TO RELATED APPLICATION

This application claims the benefit of Korean Patent Application No. 10-2005-64971, filed Jul. 18, 2005, the disclosure of which is hereby incorporated herein by reference in its entirety.

BACKGROUND OF THE INVENTION

1. Field of the Invention

The present invention relates to optical inspection tools and methods of using the tools and, more particularly, to an optical inspection tool including a lens unit with at least a pair of beam paths therein and methods of detecting surface defects of a substrate using the optical inspection tool.

2. Description of Related Art

Semiconductor devices are manufactured using various individual processes performed on a substrate such as a semiconductor wafer. These processes include deposition processes for forming a material layer such as an insulating layer, a conductive layer, or a semiconductor layer; photolithography/etching processes for patterning the material layer; ion implantation processes for doping predetermined regions of the material layer or the semiconductor substrate with impurities; chemical mechanical polishing processes for planarizing the surface of the material layer; and cleaning processes for removing contaminants remaining on the semiconductor substrate or the material layer.

During manufacture, the surface of the substrate on which there processes are performed may have an abnormal surface profile due to undesired defects such as particles and/or scratches. These particles or the scratches may exacerbate defect formation in future processes, thereby potentially reducing yield or reliability of the semiconductor device. Therefore, precise measurement and analysis of the surface defects of the semiconductor device is required to improve yield. These surface defects may be detected using an optical inspection tool that employs a light source and a lens.

FIG. 1 is a schematic view of a conventional bright field optical inspection tool. Such an inspection tool includes a lens module 5, a beam splitter 3 disposed on the lens module 5, and a camera 7 disposed on the beam splitter 3. A light source 9 is installed at one side of the beam splitter 3, and the light source 9 generates a first incident light 9a parallel to a surface of a substrate 1, which is located under the lens module 5. The beam splitter 3 converts the first incident light 9a into a second incident light 9b, which is perpendicular to the substrate 1, and the second incident light 9b is irradiated onto the substrate 1 or the lens module 5 at an incident angle of 0°. As a result, a normal reflected light 9r reflected at an angle equal to the incident angle is generated on the surface of the substrate 1. A portion 9r' of the reflected light 9r is irradiated into the camera 7 through the beam splitter 3 to provide a bright field, and the remainder 9r" of the reflected light 9r is reflected by the beam splitter 3 in a direction parallel to the surface of the substrate 1 where it does not to contribute to the formation of the bright field.

When surface defects SD such as particles or scratches exist on the surface of the substrate 1, the second incident light 9b is irregularly reflected from the defect surfaces to generate scattered light 9s. That is, the surface defects SD provide an abnormal reflected light, such as the scattered light 9s, which results in formation of dark images in the bright field.

The resolution R of the dark image corresponding to the surface defects SD may be expressed by the following equation 1.

$$R \propto \lambda NA \quad \text{(equation 1)}$$

where "$\lambda$" represents a wavelength of the light 9b incident on the substrate, and "NA" represents a numerical aperture of the lens module 5. The numerical aperture is approximately proportional to a diameter DM of the lens module 5, and approximately inversely proportional to a distance d between the lens module 5 and the substrate 1 (i.e., a focal distance of the lens module 5).

In addition, the numerical aperture NA may be expressed by the following equation 2.

$$NA = n \times \sin(\theta) \quad \text{(equation 2)}$$

where "n" is the index of refraction (which is equal to 1 for air) and "$\theta$" represents an angle between a central vertical axis of the lens module 5 and a light beam irradiated from a focal point of the lens module 5 toward an edge of the lens module 5.

To improve performance of the lens module 5, the resolution R should be reduced so that smaller surface defects can be resolved. That is, as can be seen from the equations 1 and 2, "$\theta$" should be increased in order to enhance the resolution R. In other words, to improve the resolution R, the diameter DM of the lens module 5 should be increased or the focal distance d of the lens module 5 should be reduced.

The conventional optical inspection tool shown in FIG. 1 does not have any limitations in reducing the focal distance d of the lens module 5. Therefore, it may be easy to enhance the resolution of the conventional optical inspection tool using a bright field. However, because the conventional optical inspection tool employing the bright field uses an incident light vertical to the surface of the substrate to generate images of defects, it may be difficult to obtain an image corresponding to the shape of the defects. For example, groove-shaped defects having flat surfaces may not provide high resolution images even though a conventional optical inspection tool adopting a bright field is used. All surface defects including particles and scratches as well as groove-shaped defects may be easily detected by an optical inspection tool employing an oblique illumination angle, i.e., an optical inspection tool using a dark field.

FIG. 2 is a schematic view of a conventional optical inspection tool using a dark field. Referring to FIG. 2, the conventional optical inspection tool includes a lens module 13, a lens housing 17 surrounding the lens module 13, and a camera 15 installed on the lens module 13. A light source 19 and a light trap 21 are installed on either side of the lens module 13, respectively. The light source 19 generates an incident light beam 19a that contacts the substrate 11 disposed under the lens module 13 at an oblique angle $\alpha$ (i.e. less than 90°). The light trap 21 is disposed at a position that may receive a reflected light beam 19n specularly reflected from the surface of the substrate 11.

A reflective angle $\beta$ of the specularly reflected light beam 19n should be equal to the incident angle $\alpha$. Therefore, when no defect exists on the surface of the substrate 11, the camera 15 provides a dark field since no light is scattered and thus irradiated into the lens module 13. That is, when surface defects 11a such as particles or scratches exist on the surface of the substrate 11, the incident light 19a is irregularly reflected due to the surface defects 11a. At least a portion of the resulting scattered light 19s is irradiated up into the lens module 13 to generate a relatively bright image in the dark field.

The resolution R of the bright image corresponding to the surface defects 11a may also be expressed by the equation 1. And as stated earlier, the resolution R of detectible surface defects 11a is approximately inversely proportional to a distance d (i.e., a focal distance) between the lens module 13 and the substrate 11, and approximately proportional to a diameter DM of the lens module 13. Therefore, to improve the resolution R, the distance d between the lens module 13 and the substrate 11 should be reduced or the diameter DM of the lens module 13 should be increased (or both). However, in the conventional optical inspection tool shown in FIG. 2, there are physical limitations in reducing the focal distance d or increasing the diameter DM of the lens module 13. That is, the lens module 13 and the lens housing 17 surrounding the lens module 13 may block the obliquely directed incident light 19a if the lens module 13 is placed too close to the substrate 11, or if the module is widened.

And although the prior art has presented examples of methods to detect defects using novel inspection tools (e.g. U.S. Pat. No. 5,631,733 to Henley, entitled "Large Area Defect Monitor Tool for Manufacture of Clean Surfaces"), drawbacks still exist. Accordingly, it is desired to have improved tools and methods suitable for oblique illumination with improved resolution.

SUMMARY OF THE INVENTION

An embodiment of the invention provides optical inspection tools that are suitable for improvement of resolution even with an oblique illumination. Methods of detecting surface defects of a substrate using these tools are described.

Another embodiment of the invention provides optical inspection tools that are suitable to precisely locate a substrate at a focal distance of a lens module and methods of detecting surface defects of a substrate using the same.

In one aspect, the invention is directed to optical inspection tools. The optical inspection tools include a lens unit and a chuck located below the lens unit. The chuck provides a place on which a substrate is loaded, and the lens unit includes at least a pair of beam paths therein. The beam paths do not have a function of a lens. Thus, light passing through the beam paths travel straight. A camera is disposed on the lens unit. The camera converts lights that reach the camera through the lens unit into an image.

In some embodiments of the present invention, at least the pair of beam paths may include at least one first beam path and at least one second beam path which are symmetrical to each other with respect to a vertical central axis of the lens unit. Each of the beam paths may be an empty space that penetrates a portion of at least one lens of a plurality of lenses constituting the lens unit. In this case, each of the beam paths may have an open slit shape or a hole shape.

In other embodiments, each of the beam paths may include a flat region formed at a portion of at least one lens of a plurality of lenses constituting the lens unit. The flat region may have an upper surface and a lower surface which are parallel to each other.

In still other embodiments, a main light source and a light trap may be fixed to the lens unit. The main light source may be installed to provide a main oblique incident light beam irradiated on the substrate through the first beam path, and the light trap may be installed to receive a main reflected light beam reflected from a surface of the substrate through the second beam path. Furthermore, an auxiliary light source and a sensing unit may be fixed to the lens unit. The auxiliary light source may provide an auxiliary oblique incident light irradiated onto the substrate, and the sensing unit may sense an auxiliary reflected light beam reflected from the substrate by the auxiliary oblique incident light. Therefore, a position where the auxiliary reflected light beam is irradiated onto the sensing unit may change according to a distance between the substrate and the lens unit. As a result, it is possible to position the substrate at a predetermined distance from the lens unit by changing the distance between the substrate and the lens unit until the auxiliary reflected light beam is irradiated onto a desired sensor of a plurality of sensors constituting the sensing unit.

In other embodiments, a beam splitter may be interposed between the lens unit and the camera, and a main light source may be installed to provide a main incident light beam irradiated to the beam splitter. The beam splitter converts a portion of the main incident light beam into a main vertical incident light beam irradiated onto the substrate. In this case, an auxiliary light source and a sensing unit fixed to the lens unit may be additionally installed. The auxiliary light source may provide an auxiliary oblique incident light beam irradiated onto the substrate through the first beam path, and the sensing unit may sense an auxiliary reflected light beam reflected from the surface of the substrate through the second beam path. As a result, a position where the auxiliary reflected light beam is irradiated onto the sensing unit may change according to a distance between the substrate and the lens unit.

In another aspect, the invention is directed to methods of detecting surface defects of a substrate. The methods include providing a substrate and loading the substrate onto a chuck. A lens unit is disposed over the chuck. The lens unit includes at least one first beam path and at least one second beam path therein. The first and second beam paths allow light to travel straight. The substrate is positioned at a focal distance of the lens unit. An image corresponding to a surface profile of the substrate is then generated using a camera installed on the lens unit.

In still other embodiments, positioning the substrate at a focal distance of the lens unit may include irradiating an auxiliary oblique incident light beam onto the substrate using an auxiliary light source fixed to the lens unit to generate an auxiliary reflected light beam traveling toward a sensing unit fixed to the lens unit, and changing a distance between the substrate and the lens unit until the auxiliary reflected light beam is irradiated onto a specific sensor of the sensing unit. The auxiliary oblique incident light beam may be irradiated through the first beam path, and the auxiliary reflected light beam may be reflected through the second beam path. In addition, the distance between the substrate and the lens unit may be changed by moving at least one of the substrate and the lens unit upwardly or downwardly.

In yet other embodiments, generating the image may include irradiating a main oblique incident light beam onto the substrate through the first beam path to generate a main reflected light beam passing through the second beam path, and irradiating light scattered from the surface of the substrate to the camera through the lens unit during irradiation of the main oblique incident light beam. The main oblique incident light beam may be provided using a main light source fixed to the lens unit, and the main reflected light beam may be trapped by a light trap fixed to the lens unit.

In still other embodiments, generating the image may include irradiating a main vertical incident light beam onto the substrate using a beam splitter installed between the lens unit and the camera to generate a main vertical reflected light beam and scattered light from the surface of the substrate, and irradiating the main vertical reflected light beam and the scattered light to the camera through the lens unit and the beam splitter. The main vertical incident light beam may be provided using a main light source fixed to the lens unit.

BRIEF DESCRIPTION OF THE DRAWINGS

The foregoing and other objects, features and advantages of the invention will be apparent from the more detailed description of preferred embodiments of the invention, as illustrated in the accompanying drawing. The drawings are not necessarily to scale, emphasis instead being placed upon illustrating the principles of the invention.

DETAILED DESCRIPTION OF THE INVENTION

Figure 1:
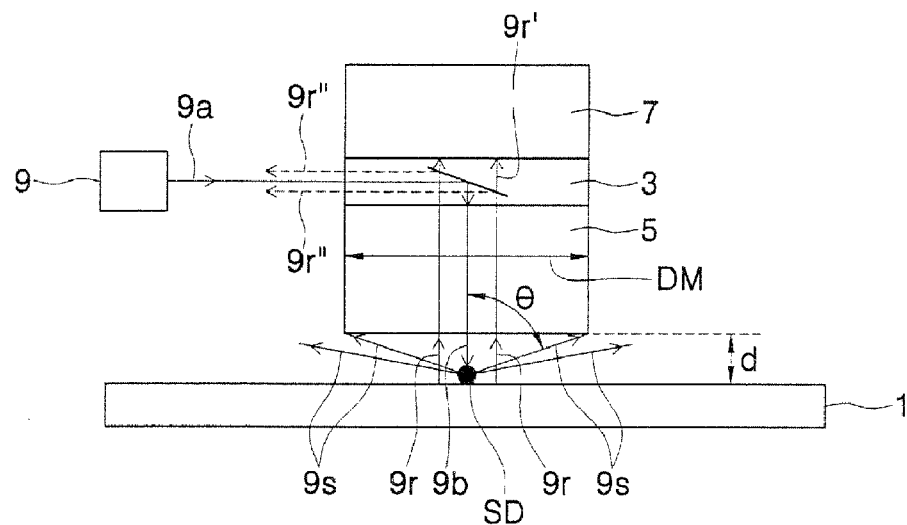
FIG. 1 is a schematic view of a conventional optical inspection tool using a bright field.
Figure 2:
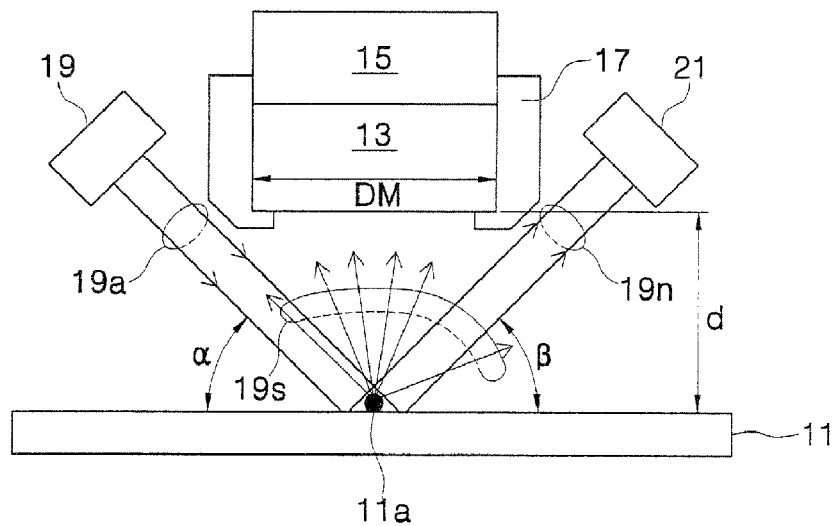
FIG. 2 is a schematic view of a conventional optical inspection tool using a dark field.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, sizes and thicknesses of layers and regions may be exaggerated for clarity. Like reference numerals designate like elements throughout the specification.

Figure 3:
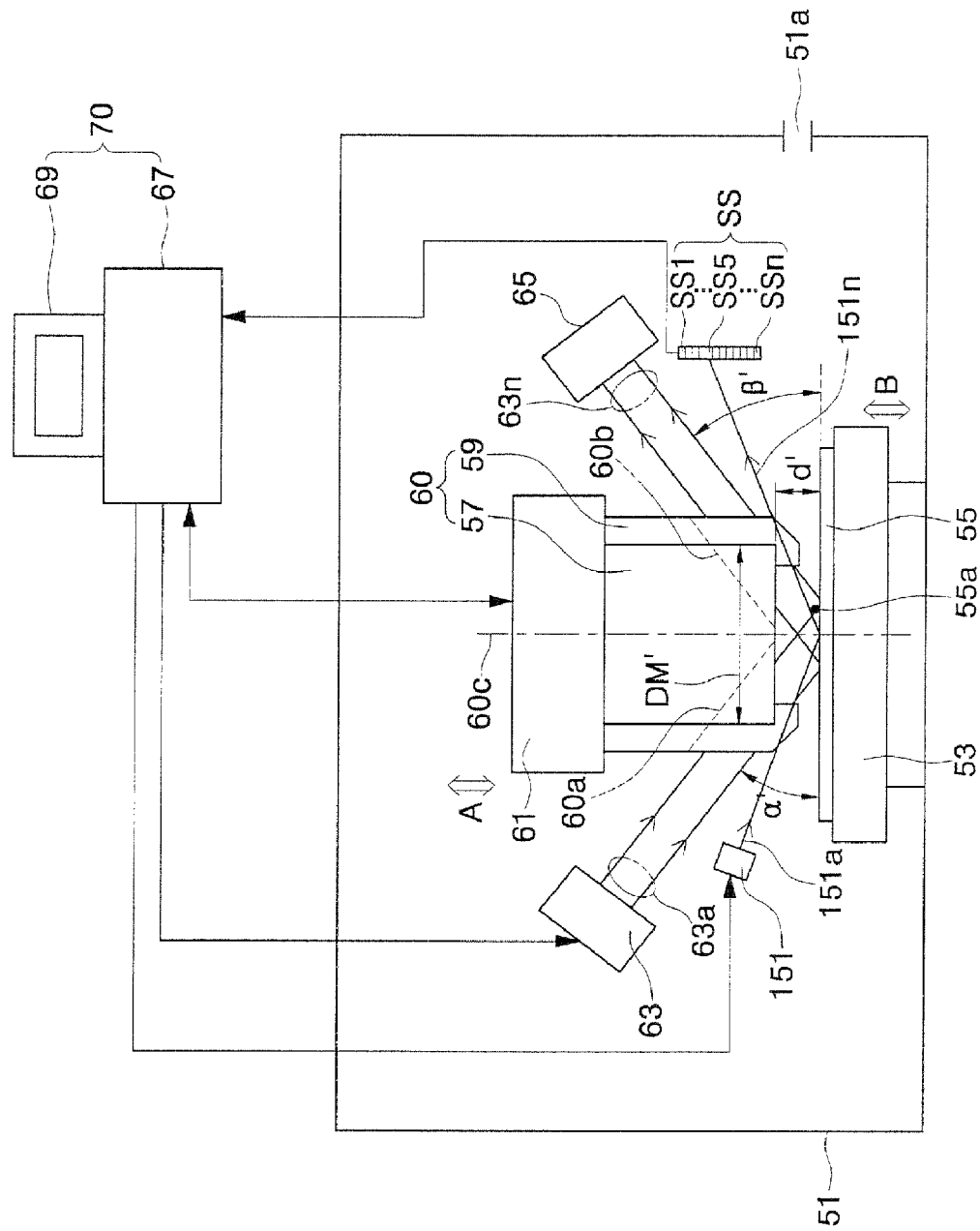
FIG. 3 is a schematic view of an optical inspection tool according to an embodiment of the present invention.
Figure 4A:
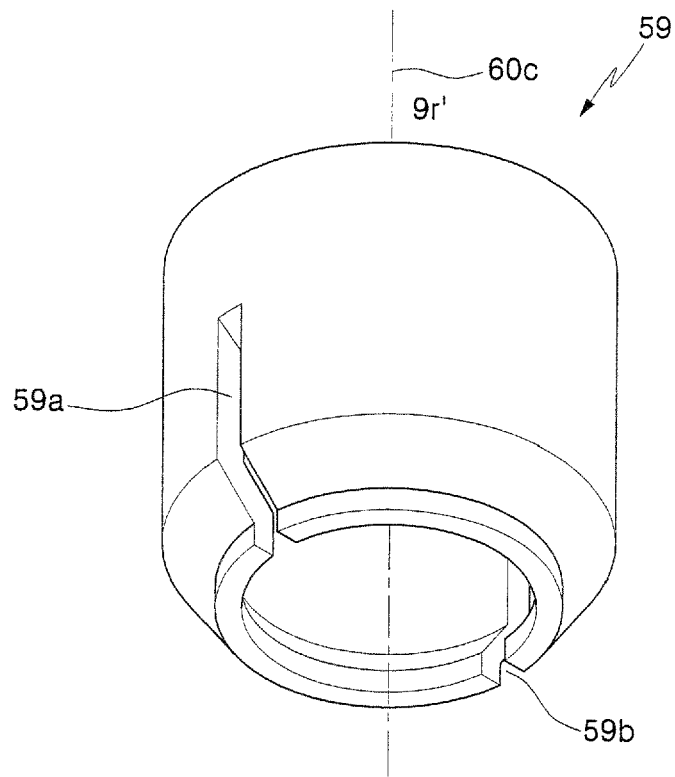
FIG. 4A is a perspective view of the lens housing of FIG. 3.
Figure 4B:
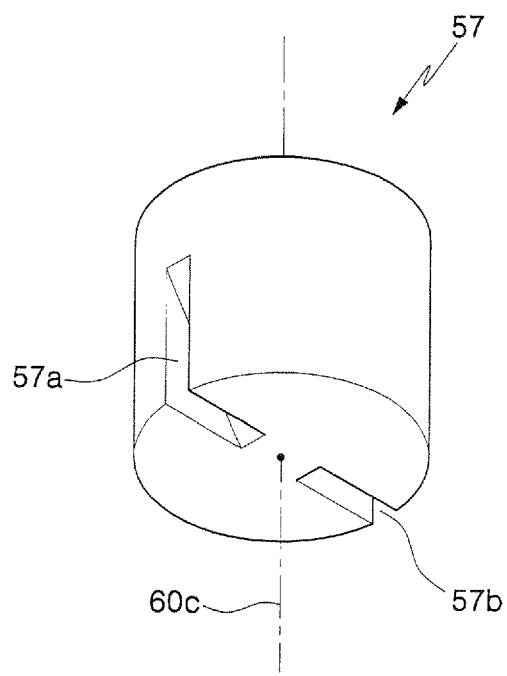
FIG. 4B is a perspective view illustrating an exemplary embodiment of the lens module of FIG. 3.

FIG. 3 is a schematic view of an optical inspection tool in accordance with an embodiment of the present invention, and FIGS. 4A and 4B are perspective views illustrating a lens housing and a lens module of FIG. 3, respectively.

Referring to FIGS. 3, 4A and 4B, a chuck 53 is disposed in a case 51 that provides a sealed space. The chuck 53 provides a place on which a substrate 55 such as a semiconductor wafer is loaded. The substrate 55 may be loaded or unloaded through a slit-shaped opening 51a penetrating a portion of a sidewall of the case 51.

A lens unit 60 is installed over the chuck 53. The lens unit 60 may include a lens module 57 and a lens housing 59 surrounding a sidewall of the lens module 57. The lens module 57 may comprise a plurality of lenses. For example, the lens module 57 may have at least one convex lens and at least one concave lens. In addition, the lens module 57 may have a cylindrical shape as shown in FIG. 4B. The lens housing 59 may extend to cover an edge of a bottom surface of the lens module 57.

The lens unit 60 may include at least a pair of beam paths, for example, first and second beam paths 60a and 60b therein.

In an embodiment of the present invention, the first and second beam paths 60a and 60b may be first and second empty spaces passing through the lens unit 60. In this case, the first empty space 60a functions as a path of a main oblique incident light 63a irradiated toward the substrate 55 from a main light source 63 installed at one side of the lens unit 60. An incident angle α' of the main oblique incident light 63a is an oblique angle less than 90° as shown in FIG. 3. Therefore, the first empty space 60a may pass through a lower corner region of the lens unit 60. In other words, the first empty space 60a may pass through a lower corner region of the lens housing 59 and also a portion of at least a lowermost lens of a plurality of lenses constituting the lens module 57. In this case, the first empty space 60a may include a first housing opening 59a (see FIG. 4A) passing through the lens housing 59 and a first lens opening 57a (see FIG. 4B) passing through the lens module 57. That is, the lens module 57 is inserted into the lens housing 59 so that the first lens opening 57a is aligned with the first housing opening 59a.

The second empty space 60b functions as a path of a main reflected light 63n reflected from the substrate 55 while the main oblique incident light 63a is irradiated onto the substrate 55 through the first empty space 60a. In this case, a reflecting angle β' of the main reflected light 63n is equal to the incident angle α'. Therefore, the first and second empty spaces 60a and 60b are preferably symmetrical to each other with respect to a vertical axis 60c passing through the center of the lens unit 60, and the second empty space 60b may also include a second housing opening 59b (see FIG. 4A) passing through the lens housing 59 and a second lens opening 57b (see FIG. 4B) passing through the lens module 57 like the first empty space 60a. As a result, the second housing opening 59b may be symmetrical to the first housing opening 59a with respect to the central axis 60c, and the second lens opening 57b may be symmetrical to the first lens opening 57a with respect to the central axis 60c. In this case, when the first lens opening 57a is aligned with the first housing opening 59a, the second lens opening 57b may also be aligned with the second housing opening 59b. The main reflected light 63n passing through the second empty space 60b is trapped by a light trap 65 installed at the other side of the lens unit 60 from the main light source. The main light source 63 and the light trap 65 may be fixed to the lens unit 60. Thus, the main light source 63 and the light trap 65 may move together with the lens unit 60.

According to the above described embodiment, although a distance d' between the lens module 57 and the substrate 55 decreases or a diameter DM' of the lens module 57 increases, the main oblique incident light 63a may be regularly irradiated onto the substrate 55 without any blocking loss because of the presence of the first and second empty spaces 60a and 60b, and the main reflected light 63n from the substrate 55 may also reach the light trap 65 without any blocking loss. However, the first and second empty spaces 60a and 60b may degrade a function of the lens module 57 since the empty spaces 60a and 60b reduce its net volume. Nevertheless, the resolution of the lens module 57 may be remarkably improved as compared to the conventional art. This is because an increase rate of the resolution according to an increase in the diameter DM' of the lens module 57 and/or a reduction in the focal distance of the lens module 57 may be greater than a decrease rate of resolution that is due to the presence of the first and second empty spaces 60a and 60b.

In other embodiments, the first empty space 60a may include only the first housing opening 59a. Similarly, the second empty space 60b may also include only the second housing opening 59b. In this case, the first and second empty spaces 60a and 60b do not cause any degradation of function of the lens module 57.

In still other embodiments, the lens unit 60 may include a plurality of first beam paths and a plurality of second beam paths corresponding to the first beam paths. That is, the lens unit 60 may include a plurality of first empty spaces and a plurality of second empty spaces corresponding to the first empty spaces. In this case, a plurality of main light sources may be installed instead of the single main light source 63, and a plurality of light traps may be installed instead of the single light trap 65.

The incident angle α' of the main oblique incident light 63a may be changed according to the configuration and type of surface defects to be inspected. In this case, it may be preferable that the first and second empty spaces 60a and 60b have open slit-shaped configurations as shown in FIGS. 4A and 4B when considering the variation of the incident angle α' and the reflecting angle β'.

When surface defects 55a exist on the substrate 55, scattered light irregularly reflected from the surface defects 55a may be generated when the main oblique incident light 63a is irradiated onto the substrate 55. Then a portion of the scattered light is irradiated toward the lens module 57. The lens module 57 concentrates the scattered light, which is converted into an image corresponding to the surface defects 55a using a camera 61, which includes a charge coupled device or a CMOS image sensor (CIS) attached on the lens module 57.

In still other embodiments, an auxiliary light source 151 and a sensing unit SS that are fixed to the lens unit 60 may be additionally provided. The auxiliary light source 151 provides an auxiliary oblique incident light 151a irradiated onto the substrate 55. The auxiliary oblique incident light 151a may be irradiated through the first beam path, i.e., the first empty space 60a. An incident angle of the auxiliary oblique incident light 151a may be different from the incident angle α' of the main oblique incident light 63a. When the auxiliary oblique incident light 151a is irradiated, an auxiliary reflected light 151n reflected from the surface of the substrate 55 is generated and irradiated toward the sensing unit SS.

The sensing unit SS may include a plurality of sensors, for example, "n"-number of sensors SS1, SS2, . . . , SSn, which may be installed at different heights form each other. Therefore, while the auxiliary oblique incident light 151a is irradiated onto the substrate 55, a position where the auxiliary reflected light 151n is irradiated onto the sensing unit SS may change according to a distance between the substrate 55 and the lens module 57. For example, the auxiliary reflected light 151n may pass through a region under the sensing unit SS when the distance between the substrate 55 and the lens module 57 increases. On the contrary, the auxiliary reflected light 151n may pass through a region over the sensing unit SS when the distance between the substrate 55 and the lens module 57 decreases. This is because the auxiliary light source 151 and the sensing unit SS are fixed to the lens unit 60 to move together with the lens module 57, as described above.

If the distance between the substrate 55 and the lens module 57 is changed until the auxiliary reflected light 151n is irradiated onto a specific sensor of the sensors SS1, . . . , SSn, the distance between the substrate 55 and the lens module 57 may be always adjusted to have a specific value. In other words, the auxiliary light source 151 and the sensing unit SS may be used as a focus controller of the lens module 57. The distance between the substrate 55 and the lens module 57 may be changed by moving at least one of the chuck 53 and the lens unit 60 upwardly or downwardly. The lens unit 60 including the lens module 57 may be installed to be movable upwardly and downwardly as shown by an arrow A of FIG. 3, and the chuck 53 may be installed to be movable upwardly and downwardly as shown by an arrow B of FIG. 3.

The auxiliary oblique incident light 151a may have a beam size less than that of the main oblique incident light. When the beam size of the auxiliary oblique incident light 151a is reduced, the distance between the substrate 55 and the lens module 57 may be precisely controlled. As a result, when the beam size of the auxiliary oblique incident light 151a is reduced, the substrate 55 may be precisely positioned at a focal distance of the lens module 57.

In the event that surface defects of the substrate 55 are detected using the main light source 63 and the light trap 65 after positioning the substrate 55 at the focal distance of the lens module 57 using the focus controller, image resolution of the surface defects may be more enhanced.

A controller 70 may be installed outside the case 51. The controller 70 may include a central processing unit 67 and a monitor 69. The central processing unit 67 may analyze image data generated by the camera 61 and may control the operation of the main light source 63. In addition, the central processing unit 67 may display the analyzed result of the image data through the monitor 69 so that an operator may recognize the analyzed result. Further, the central processing unit 67 controls the operation of the auxiliary light source 151 and detects whether the auxiliary reflected light 151n is irradiated onto a desired sensor of the sensors SS1, . . . , SSn.

Figure 4C:
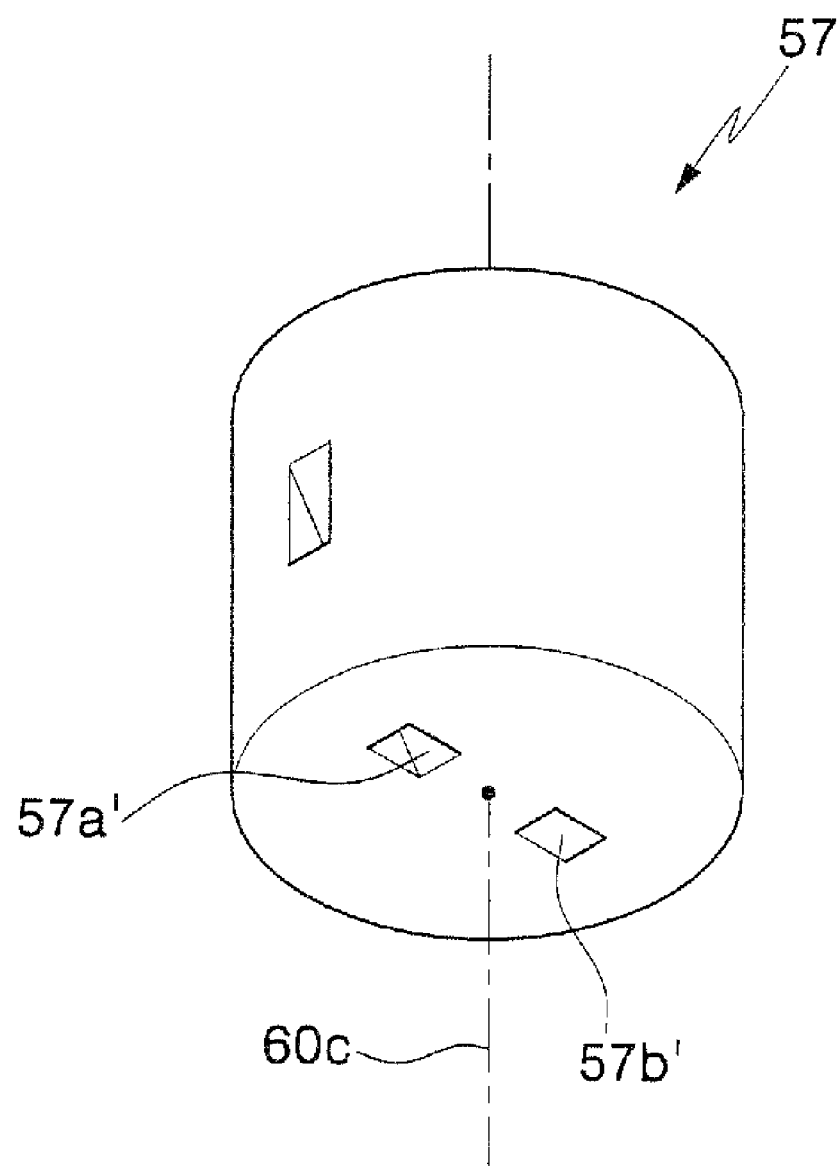
FIG. 4C is a perspective view illustrating another exemplary embodiment of the lens module of FIG. 3.

The first and second lens openings 57a and 57b may have various shapes different from the open slit shape as shown in FIGS. 4A and 4B. For example, when the main oblique incident light 63a corresponds to a spot-shaped beam irradiated at a fixed incident angle, the first and second beam paths 60a and 60b may include a first lens opening 57a' and a second lens opening 57b' passing through the inside portions of the lens module 57, respectively, as shown in FIG. 4C. That is, the first and second lens openings 57a' and 57b' may have a hole shape.

In further embodiments, the first and second beam paths 60a and 60b may have different shapes from the lens openings 57a, 57a', 57b and 57b' of FIGS. 4B and 4C, as shown in FIGS. 4D to 4K.

Figure 4D:
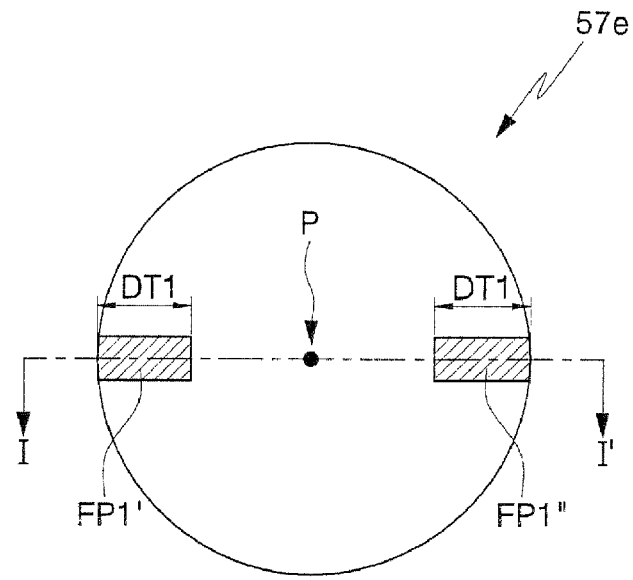
FIG. 4D is a plan view illustrating an exemplary embodiment of a convex lens employed in the lens module of FIG. 3.
Figure 4E:
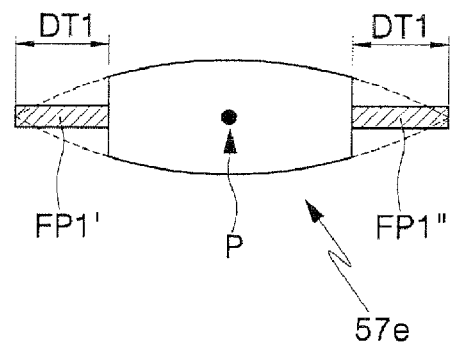
FIG. 4E is a cross-sectional view taken along line I-I' of FIG. 4D.

FIG. 4D is a plan view illustrating an exemplary embodiment of at least one convex lens of a plurality of lenses constituting the lens module 57 of FIG. 3, and FIG. 4E is a cross-sectional view taken along line I-I' of FIG. 4D.

Referring to FIGS. 4D and 4E, the convex lens 57e may include first and second flat regions FP1' and FP1", which are provided at both edges thereof, respectively. The first and second flat regions FP1' and FP1" may be symmetrical to each other with respect to a central point P of the convex lens 57e and may be in contact with the circumference of the convex lens 57e. FIGS. 4D and 4E also show a first width DT1 of the flat regions FP1' and FP1". In addition, each of the first and second flat regions FP1' and FP1" has an upper surface and a lower surface that are parallel to each other. Dashed lines in FIG. 4E show where the curved lens surface would be were it not for the flat regions. Therefore, the first and second flat regions FP1' and FP1" do not have a function of a lens for refracting light. In other words, light that passes through the flat regions FP1' and FP1" travels straight, though it may be laterally shifted upon entering and exiting the flat region. A more accurate description may include that the light travels without a net angular deviation.

In conclusion, the first and second flat regions FP1' and FP1" may be employed instead of the first and second lens openings 57a and 57b shown in FIG. 4B.

Figure 4F:
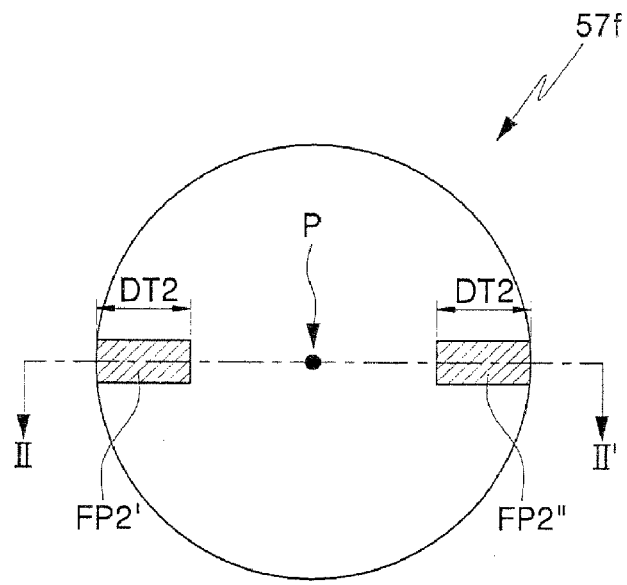
FIG. 4F is a plan view illustrating an exemplary embodiment of a concave lens employed in the lens module of FIG. 3.
Figure 4G:
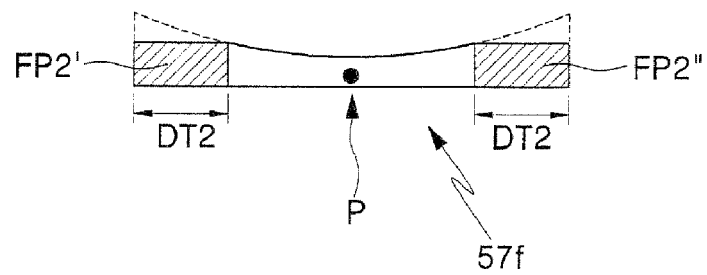
FIG. 4G is a cross-sectional view taken along line II-II' of FIG. 4F.

FIG. 4F is a plan view illustrating an exemplary embodiment of at least one concave lens of a plurality of lenses constituting the lens module 57 of FIG. 3, and FIG. 4G is a cross-sectional view taken along line II-II' of FIG. 4F.

Referring to FIGS. 4F and 4G, the concave lens 57f may include first and second flat regions FP2' and FP2", which are provided at both edges thereof, respectively. The first and second flat regions FP2' and FP2" may be symmetrical to each other with respect to a central point P of the concave lens 57f and may be in contact with the circumference of the concave lens 57f. In addition, each of the first and second flat regions FP2' and FP2" has an upper surface and a lower surface that are parallel to each other. Dashed lines in FIG. 4G show where the curved lens surface would be were it not for the flat regions. Therefore, the first and second flat regions FP2' and FP2" do not have a function of a lens for refracting light. In other words, light that passes through the flat regions FP2' and FP2" travels straight, though it may be laterally shifted upon entering and exiting the flat region, as mentioned earlier. As a result, the first and second flat regions FP2' and FP2" may be employed instead of the first and second lens openings 57a and 57b shown in FIG. 4B.

When the lens module 57 of FIG. 3 includes the convex lens 57e and the concave lens 57f, the first width DT1 of the flat regions FP1' and FP1" of the convex lens 57e may be different from a second width DT2 of the flat regions FP2' and FP2" of the concave lens 57f. For example, when the convex lens 57e is stacked on the concave lens 57f, the first width DT1 may be less than the second width DT2. In this case, the first flat regions FP1' and FP2' and the second flat regions FP1" and FP2" may be provided at positions corresponding to the first and second lens openings 57a and 57b of FIG. 4B, respectively. As a result, the flat regions FP1', FP1", FP2' and FP2" may provide paths for the main oblique incident light 63a and the main reflected light 63n.

Figure 4H:
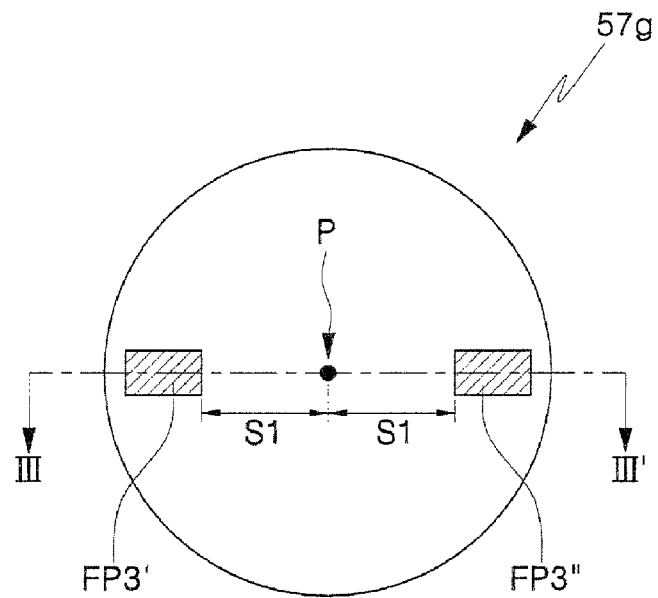
FIG. 4H is a plan view illustrating another exemplary embodiment of a convex lens employed in the lens module of FIG. 3.
Figure 4I:
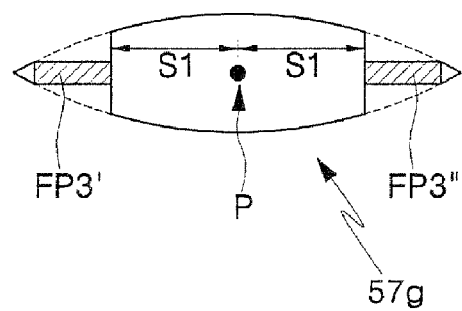
FIG. 4I is a cross-sectional view taken along line III-III' of FIG. 4H.

FIG. 4H is a plan view illustrating another exemplary embodiment of at least one convex lens of a plurality of lenses constituting the lens module 57 of FIG. 3, and FIG. 4I is a cross-sectional view taken along line III-III' of FIG. 4H.

Referring to FIGS. 4H and 4I, the convex lens 57g may include first and second flat regions FP3' and FP3", which are provided at both edges thereof, respectively. The first and second flat regions FP3' and FP3" may be symmetrical to each other with respect to a central point P of the convex lens 57g and may be spaced apart from the circumference of the convex lens 57g. FIGS. 4H and 4I also show a first distance S1 between the flat regions FP3' and FP3". In addition, each of the first and second flat regions FP3' and FP3" have an upper surface and a lower surface that are parallel to each other. Dashed lines in FIG. 4I show where the curved lens surface would be were it not for the flat regions. Therefore, the first and second flat regions FP3' and FP3" do not have a function of a lens for refracting light. In other words, light that passes through the flat regions FP3' and FP3" travels straight, though it may be laterally shifted upon entering and exiting the flat region, as mentioned earlier. As a result, the first and second flat regions FP3' and FP3" may also be employed instead of the first and second lens openings 57a' and 57'b shown in FIG. 4C.

Figure 4J:
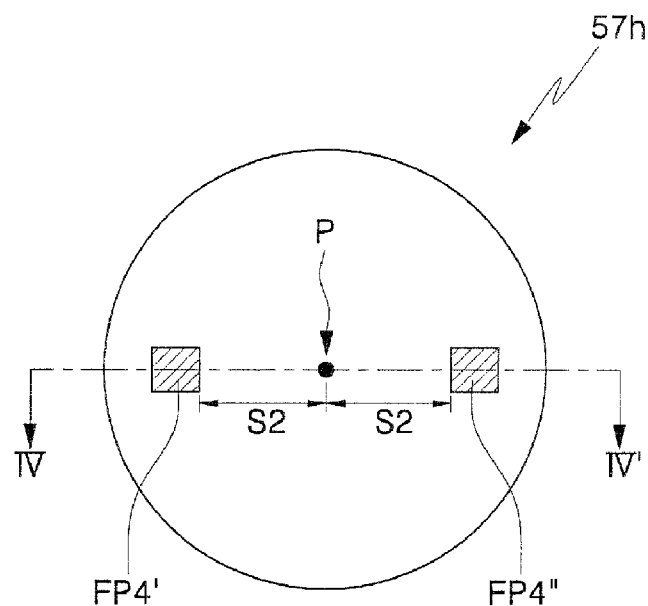
FIG. 4J is a plan view illustrating another exemplary embodiment of a concave lens employed in the lens module of FIG. 3.
Figure 4K:
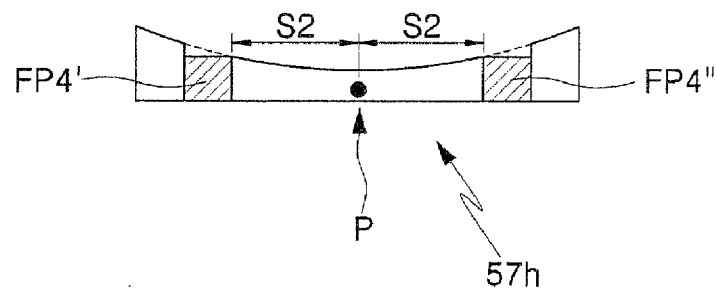
FIG. 4K is a cross-sectional view taken along line IV-IV' of FIG. 4J.

FIG. 4J is a plan view illustrating still another exemplary embodiment of at least one concave lens of a plurality of lenses constituting the lens module 57 of FIG. 3, and FIG. 4K is a cross-sectional view taken along line IV-IV' of FIG. 4J.

Referring to FIGS. 4J and 4K, the concave lens 57h may include first and second flat regions FP4' and FP4", which are provided at both edges thereof, respectively. The first and second flat regions FP4' and FP4" may be symmetrical to each other with respect to a central point P of the concave lens 57h and may be spaced apart from the circumference of the concave lens 57h. In addition, each of the first and second flat regions FP4' and FP4" have an upper surface and a lower surface that are parallel to each other. Dashed lines in FIG. 4K show where the curved lens surface would be were it not for the flat regions. Therefore, the first and second flat regions FP4' and FP4" do not have a function of a lens for refracting light. In other words, light that passes through the flat regions FP4' and FP4" travels straight, though it may be laterally shifted upon entering and exiting the flat region, as mentioned earlier. In conclusion, the first and second flat regions FP4' and FP4" may also be employed instead of the first and second lens openings 57a' and 57b' shown in FIG. 4C.

When the lens module 57 of FIG. 3 includes the convex lens 57g and the concave lens 57h, the first distance S1 between the flat regions FP3' and FP3" and the central point P of the convex lens 57g may be different from a second distance S2 between the flat regions FP4' and FP4" and the central point P of the concave lens 57h. For example, when the convex lens 57g is stacked on the concave lens 57h, the first distance S1 may be greater than the second distance S2. In this case, the first flat regions FP3' and FP4' and the second flat regions FP3" and FP4" may be provided at positions which correspond to the first and second lens openings 57a' and 57b' of FIG. 4C, respectively.

Figure 5:
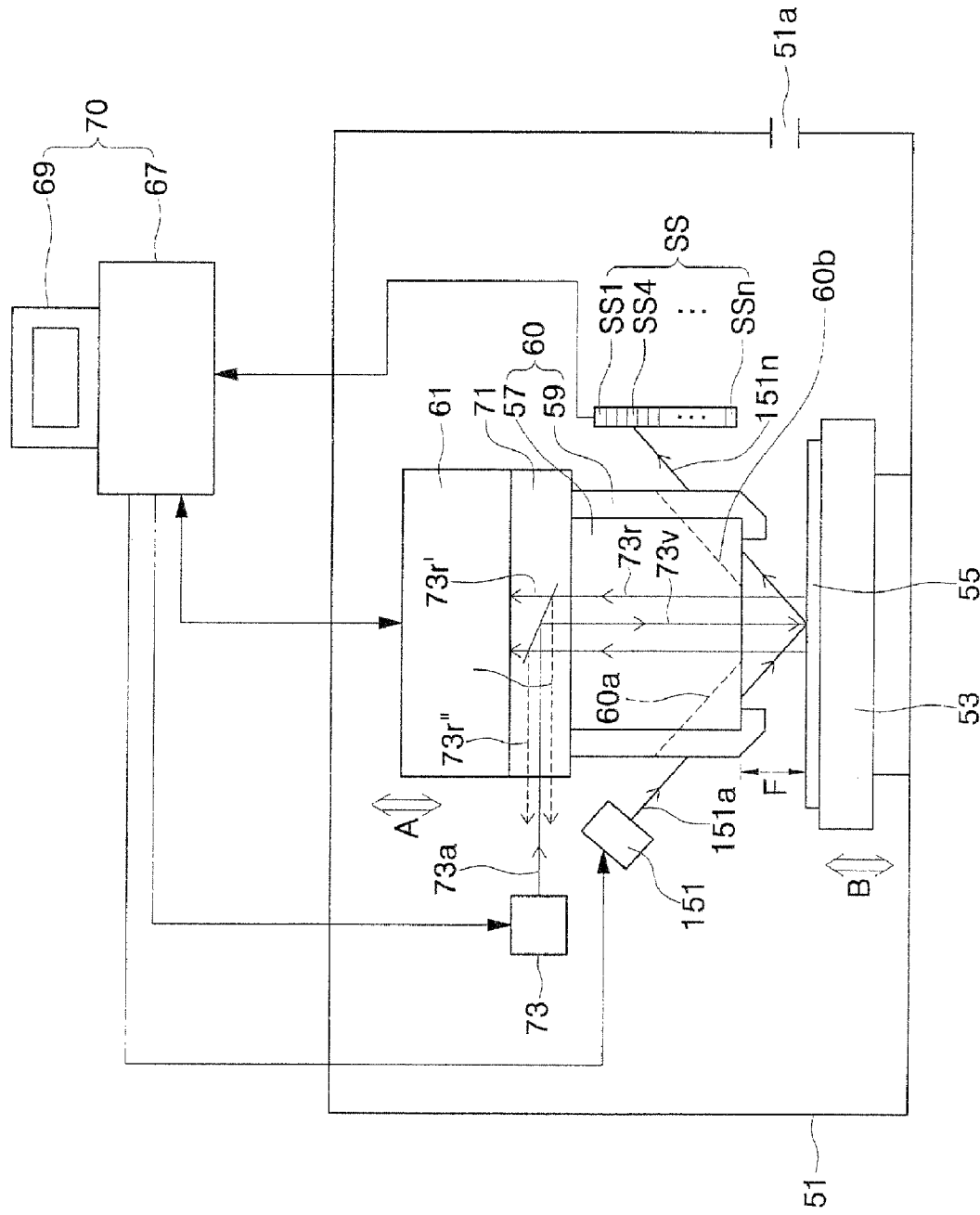
FIG. 5 is a schematic view of an optical inspection tool according to another embodiment of the present invention.

FIG. 5 is a schematic view of an optical inspection tool in accordance with another embodiment of the present invention. In the embodiments illustrated in FIGS. 3 and 5, like reference numerals designate like elements. Therefore, in the present embodiment, detail descriptions of components designated by the same reference numerals as used in the embodiment of FIG. 3 will be omitted.

Referring to FIG. 5, a beam splitter 71 may be interposed between the camera 61 and the lens unit 60. A main light source 73 fixed to the lens unit 60 is installed, and the main light source 73 provides a main incident light 73a irradiated toward the beam splitter 71. The beam splitter 71 converts the main incident light 73a into a main vertical incident light 73v perpendicular to the substrate 55. The main vertical incident light 73v is reflected from a surface of the substrate 55 to generate a main vertical reflected light 73r. A portion 73r' of the main vertical reflected light 73r passes through the lens module 57 and the beam splitter 71 to reach the camera 61, and the remaining portion 73r" of the main vertical reflected light 73r may be reflected from the beam splitter 71 to go toward the main light source 73. When surface defects exist on the substrate 55, a portion of scattered light irregularly reflected from the surface defects also passes through the lens module 57 and the beam splitter 71 to reach the camera 61 while the main vertical incident light 73v irradiates.

In addition, the optical inspection tool according to the present embodiment may include a focus controller composed of an auxiliary light source 151 and a sensing unit SS, as described with reference to FIG. 3. Hence, according to the present embodiment, the substrate 55 may be precisely positioned at a focal distance F of the lens module 57 using the focus controller, and the beam splitter 71 and the main light source 73 provide a bright field. In conclusion, according to the present embodiment, resolution of an optical inspection tool using a bright field may be enhanced.

Hereinafter, methods of detecting surface defects of a substrate using the optical inspection tools shown in FIGS. 3 and 5 will be described with reference to FIGS. 6 and 7.

Figure 6:
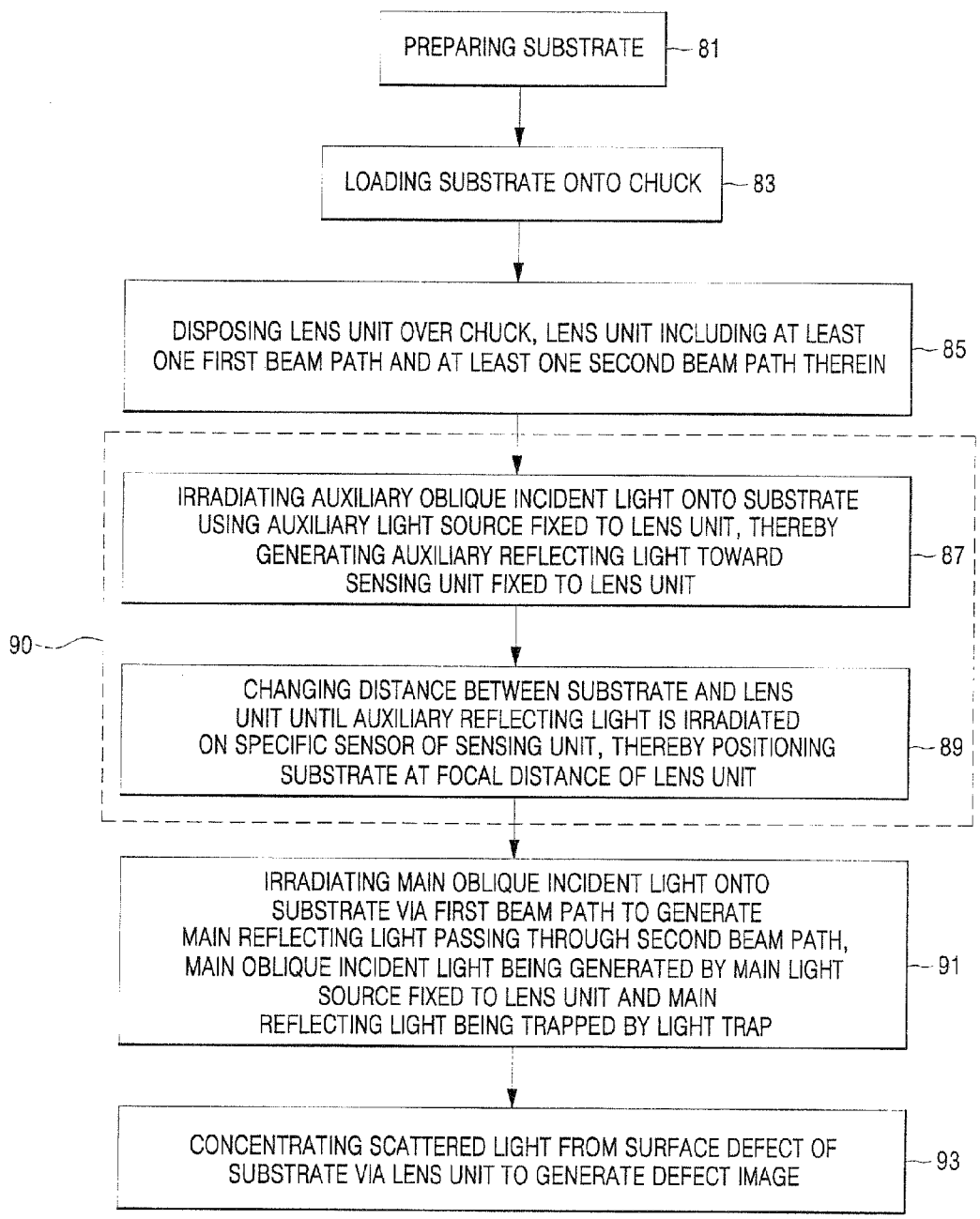
FIG. 6 is a process flowchart illustrating methods of detecting surface defects of a substrate using the optical inspection tool shown in FIG. 3.

FIG. 6 is a process flowchart illustrating methods of detecting surface defects of a substrate using the optical inspection tool of FIG. 3.

Referring to FIGS. 3 and 6, a substrate 55 such as a semiconductor wafer is provided (step 81 of FIG. 6). The substrate 55 is loaded onto a chuck 53 installed in a case 51, which provides a sealed space (step 83 of FIG. 6). The substrate 55 may be loaded through a slit-shaped opening 51a penetrating a sidewall of the case 51. A lens unit 60 is disposed over the chuck 53 (step 85 of FIG. 6). The lens unit 60 includes first and second beam paths 60a and 60b passing through therein, as described with reference to FIG. 3. In addition, the lens unit 60 may include a lens module 57 having a plurality of lenses and a lens housing 59 surrounding the sidewall of the lens module 57.

The substrate 55 may be positioned at a focal distance of the lens module 57 using the sensing unit SS and the auxiliary light source 151 fixed to the lens unit 60 (step 90 of FIG. 6). The sensing unit SS includes a plurality of sensors having different heights. In addition, when the auxiliary oblique incident light 151a is irradiated onto a focal plane of the lens module 57, the sensing unit SS is configured to have a specific sensor installed at a position at which the light reflected from the focal plane arrives.

In more detail, in order to position the substrate 55 at the focal distance of the lens module 57, the auxiliary oblique incident light 151a is irradiated onto the substrate 55 to generate an auxiliary reflected light 151n reflected from its surface (step 87 of FIG. 6). A distance between the substrate 55 and the lens module 57 is then changed until the auxiliary reflected light 151n is irradiated onto the specific sensor of the sensing unit SS (step 89 of FIG. 6). As a result, the substrate 55 may be precisely positioned at the focal distance of the lens module 57. The auxiliary oblique incident light 151a may be irradiated through the first beam path 60a of the lens unit 60. In this case, the auxiliary reflected light 151n may reach the sensing unit SS through the second beam path 60b. Thus, the substrate 55 may be precisely positioned at the focal distance of the lens module 57 due to the presence of the first and second beam paths 60a and 60b, even though the focal distance of the lens module 57 decreases or the diameter of the lens module 57 increases to enhance the resolution of the lens module 57.

Subsequently, a main oblique incident light 63a is irradiated onto the substrate 55 positioned at the focal distance of the lens module 57 (step 91 of FIG. 6). The main oblique incident light 63a may be irradiated at an incident angle $\alpha'$ less than 90° with respect to the substrate 55 through the first beam path 60a. While the main oblique incident light 63a is irradiated, a main reflected light 63n reflected from the substrate 55 is generated. The main reflected light 63n is irradiated toward a light trap 65 fixed to the lens unit 60, and the light trap 65 traps the main reflected light 63n in order to prevent the main reflected light 63n from being additionally reflected within the case 51. The main reflected light 63n corresponds to light reflected at the same angle as the incident angle $\alpha'$. That is, a reflective angle $\beta'$ of the main reflected light 63n is equal to the incident angle $\alpha'$ of the main oblique incident light 63a. The main reflected light 63n may reach the light trap 65 through the second beam path 60b.

As described above, the first and second beam paths 60a and 60b function as beam paths through which the main oblique incident light 63a and the main reflected light 63n pass. Therefore, although a distance d' between the lens module 57 and the substrate 55 decreases or a diameter DM' of the lens module 57 increases, the main oblique incident light 63a may be normally irradiated onto the substrate 55 through the first beam path 60a and the main reflected light 63n may normally arrive at the light trap 65 through the second beam path 60b. Thus, when surface defects 55a such as particles exist on the substrate 55, it is possible to greatly increase the amount of scattered light that is irregularly reflected from the surface defects 55a toward the lens module 57. In other words, the resolution of the lens module 57 may be greatly improved because of the presence of the first and second beam paths 60a and 60b.

The lens module 57 concentrates a portion of the scattered light irregularly reflected from the surface defects 55a, and the concentrated scattered light generates an image corresponding to the surface defects 55a (step 93 of FIG. 6). The image may be generated by the camera 61 installed on the lens module 57.

Figure 7:
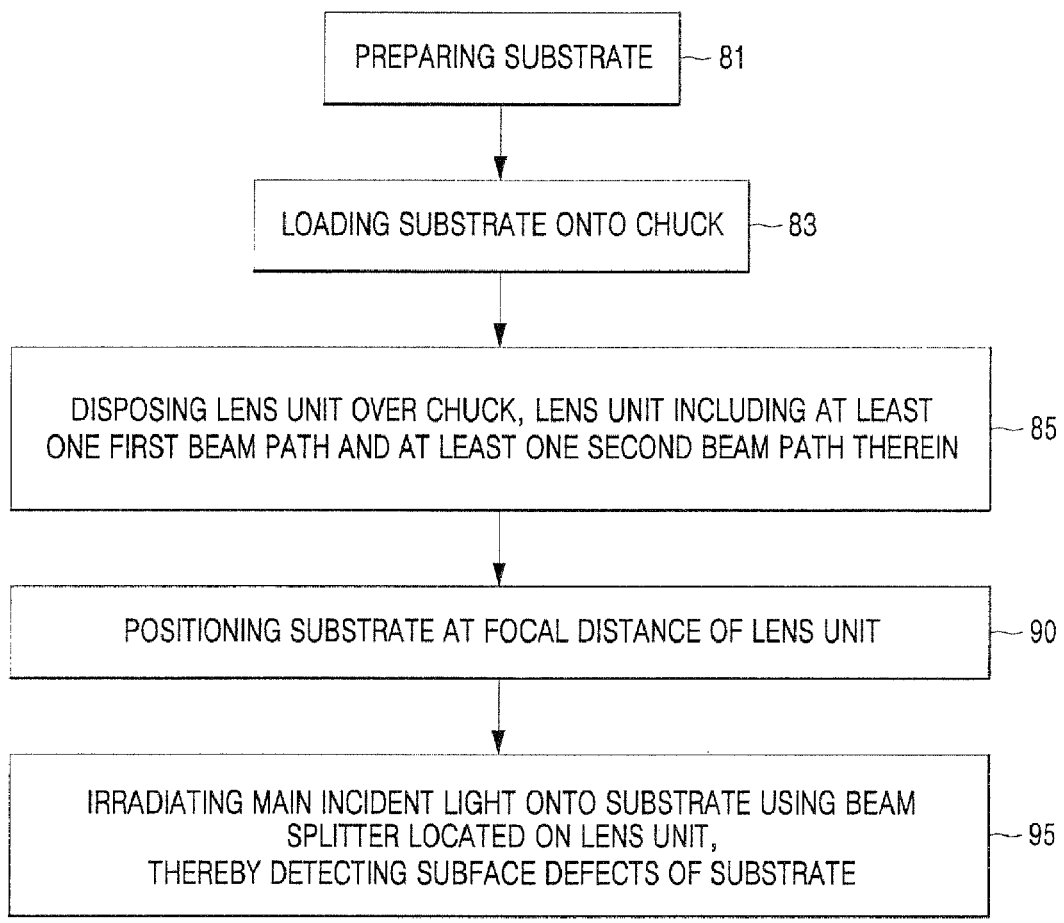
FIG. 7 is a process flowchart illustrating methods of detecting surface defects of a substrate using the optical inspection tool shown in FIG. 5.

FIG. 7 is a process flowchart illustrating methods of detecting surface defects of a substrate using the optical inspection tool shown in FIG. 5.

Referring to FIGS. 5 and 7, the substrate 55 may be precisely positioned at the focal distance F of the lens module 57 using the same method as the steps 81, 83, 85 and 90 of FIG. 6. A main incident light 73a is then irradiated toward the beam splitter 71 between the lens unit 60 and the camera 61 to detect the surface defects of the substrate 55 (step 95 of FIG. 7).

When the main incident light 73a is irradiated toward the beam splitter 71, the beam splitter 71 generates a main vertical incident light 73v perpendicular to the substrate 55. The main vertical incident light 73v generates a main vertical reflected light 73r reflected from the surface of the substrate 55. When surface defects exist on the surface of the substrate 55, the main vertical incident light 73v generates scattered light reflected from the surface defects in addition to the main vertical reflected light 73r. In this case, the main vertical reflected light 73r generates a bright field, and the scattered light is converted into a dark image corresponding to the surface defects by the lens module 57 and the camera 61.

According to the present invention as described above, first and second beam paths are provided in a lens unit having a lens module. A main oblique incident light is irradiated onto a substrate disposed under the lens unit through the first beam path, and a main reflected light reflected from the substrate passes through the second beam path. Therefore, although a focus distance of the lens module decreases or a diameter of the lens module increases, the main oblique incident light may be normally irradiated onto the substrate, and the main reflected light may normally arrive at a light trap adjacent to the lens unit. As a result, it is possible to enhance resolution of an optical inspection tool using a dark field.

In addition, an auxiliary oblique incident light and an auxiliary reflected light, which are used to position the substrate at a focal distance of the lens module, may be normally irradiated and reflected through the first and second beam paths, respectively. That is, even though a focus distance of the lens module decreases or a diameter of the lens module increases, the substrate may be precisely positioned at the focal distance of the lens module regardless of an incident angle of the auxiliary oblique incident light.

In conclusion, according to the present invention, it is possible to greatly enhance the resolution of the optical inspection tools using a bright field and a dark field.

Exemplary embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. An optical inspection tool comprising:
   a chuck for holding a substrate;
   a lens unit having a lens module and a lens housing surrounding the lens module disposed over the chuck,
   wherein the lens housing includes a light block portion and at least two empty spaces,
   wherein the lens module includes a light refracting portion and at least two light nonrefracting portions; and
   a camera installed over the lens unit to convert light reflected from the substrate that passes through the empty spaces of the lens housing and the light non-refracting, portions of the lens module into an image.

2. The optical inspection tool according to claim 1, wherein the empty spaces are first empty spaces, and the light non-refracting portions are second empty spaces.

3. The optical inspection tool according to claim 2, wherein the first and second empty spaces have an open slit shape or a hole shape.

4. The optical inspection tool according to claim 1, wherein the light non-refracting portions comprise a flat region formed in the lens module.

5. The optical inspection tool according to claim 1, further comprising:
   a main light source providing a main oblique incident light beam irradiated onto the substrate through the empty spaces and the light non-refracting portions; and
   a light trap receiving a main reflected light beam reflected from a surface of the substrate through the empty spaces and the light non-refracting portions.

6. The optical inspection tool according to claim 5, further comprising:
   an auxiliary light source providing an auxiliary oblique incident light irradiated onto the substrate; and
   a sensing unit to sense an auxiliary reflected light beam reflected from the substrate of the auxiliary oblique incident light beam,
   wherein the auxiliary light source and the sensing unit are fixed to the lens unit, and a position in the sensing unit onto which the auxiliary reflected light beam is irradiated changes according to a distance between the substrate and the lens unit.

7. The optical inspection tool according to claim 1, further comprising:
   a beam splitter interposed between the lens unit and the camera; and
   a main light source providing a main incident light beam irradiated toward the beam splitter,
   wherein the beam splitter converts a portion of the main incident light beam into a main vertical incident light beam irradiated onto the substrate.

8. The optical inspection tool according to claim 7, further comprising:
   an auxiliary light source providing an auxiliary oblique incident light beam irradiated onto the substrate through the empty spaces and the light nonrefracting portions; and
   a sensing unit to sense and an auxiliary reflected light beam reflected from a surface of the substrate through the empty spaces and the light nonrefracting portions,
   wherein the auxiliary light source and the sensing unit are fixed to the lens unit, and
   a position in the sensing unit onto which the auxiliary reflected light beam is irradiated changes according to a distance between the substrate and the lens unit.

9. An optical inspection method comprising:
   loading a substrate onto a chuck;
   disposing a lens unit-over the chuck, wherein the lens unit has a lens module and a lens housing surrounding the lens module,
   wherein the lens housing includes a light block portion and at least two empty spaces,
   wherein the lens module includes a light refracting portion and at least two light nonrefracting portions;
   positioning the substrate at a focal distance of the lens unit;
   irradiating a main incident light beam onto a surface of the substrate positioned at the focal distance to generate a main reflected light beam,
   in which the main incident light beam passes through the lens along the at least one first beam path without striking the refraction portion of the lens, and in which the main reflected light beam passes through the empty spaces of the lens housing and the light non-refracting portions of the lens; and
   generating an image corresponding to a surface profile of the substrate using a camera installed on the lens unit during irradiation of the main incident light beam.

10. The optical inspection method according to claim 9, wherein the empty spaces are first empty spaces, and the light non-refracting portions are second empty spaces.

11. The optical inspection method according to claim 10, wherein the first and second empty spaces have an open slit shape or a hole shape.

12. The optical inspection method according to claim 9, wherein the light non-refracting portions comprise flat regions in a portion of the lens.

13. The optical inspection method according to claim 9, wherein positioning the substrate at a focal distance of the lens unit comprises:
   irradiating an auxiliary oblique incident light beam onto the substrate using an auxiliary light source fixed to the lens unit, thereby generating an auxiliary reflected light beam incident on a sensing unit fixed to the lens unit; and
   changing a distance between the substrate and the lens unit so that the auxiliary reflected light beam is irradiated to a specific sensor of the sensing unit when the substrate is at the focal distance of the lens unit.

14. The optical inspection method according to claim 13, wherein the auxiliary oblique incident light beam and the auxiliary reflected light beam are reflected through the empty spaces and the light non-refracting portions.

15. The optical inspection method according to claim 13, wherein a distance between the substrate and the lens unit is changed by moving at least one of the substrate and the lens unit upwardly or downwardly.

16. The optical inspection method according to claim 9, wherein the main incident light beam is a main oblique incident light beam that is provided to pass through-the empty spaces and the light nonrefracting portions and the main reflected light beam passes through the empty spaces and the light non-refracting portions to reach a light trap fixed to the lens unit,
wherein the main oblique incident light beam is generated from a main light source fixed to the lens unit, and
wherein light scattered from the surface of the substrate during irradiation of the main oblique incident light beam is radiated to the camera through the lens unit.

17. The optical inspection method according to claim 9, wherein the main incident light beam is a main vertical incident light beam that is radiated onto the substrate through a beam splitter installed between the lens unit and the camera and the main reflected light beam is a main vertical reflected light beam that is reflected from the surface of the substrate, and
wherein light scattered from the substrate and the main vertical reflected light beam during irradiation of the main vertical incident light beam are radiated to the camera through the lens unit and the beam splitter.

18. The optical inspection method according to claim 17, wherein the main incident light beam is provided using a main light source fixed to the lens unit.

19. The optical inspection method according to claim 13, wherein a beam size of the auxiliary oblique incident light beam is smaller than that of the main incident light beam.

20. A lens unit comprising:
a lens module disposed about a vertical axis and having a lens, the lens comprising:
a light refracting portion; and
first and second oblique light non-refracting portions formed therein in symmetry to each other about the vertical axis,
wherein the first and second oblique light non-refracting portions are empty spaces penetrating the light refracting portion.

21. The lens unit of claim 20, further including a lens housing surrounding the lens module, said lens housing having first and second light transparent portions aligned, respectively, with first and second light non-refracting portions.

22. The lens unit of claim 21, wherein said first and second light non-refracting portions and first and second light transparent portions comprise empty spaces.

23. The lens unit of claim 21, the first and second light non-refracting portions including, respectively, a first empty spaces and second empty spaces adapted to simultaneously admit light from a main light sources.

24. The lens unit of claim 22, wherein the empty spaces are slit-shaped or hole-shaped.

25. The lens unit of claim 20, wherein the lens module has first and second light non-refracting portions and first and second flat regions along the light non-refracting portions, said flat regions having an upper surface and a lower surface.

26. The optical inspection tool according to claim 1,
wherein $\beta$ is greater than the difference of $\pi/2$ minus $\theta$,
where $\theta$ represents a first angle between a central vertical axis of the lens module and the light direction reflected from the substrate, and
$\beta$ represents a second angle between the horizontal direction parallel to the surface of the substrate and the light direction reflected from the substrate.

27. The optical inspection tool according to claim 1, wherein the light non-refracting portions are formed from a sidewall of the lens module to a bottom surface of the lens module penetrating the lens module.

28. The optical inspection method according to claim 9,
wherein $\beta$ is greater than the difference of $\pi/2$ minus $\theta$,
where $\theta$ represents a first angle between a central vertical axis of the lens module and the light direction reflected from the substrate, and
$\beta$ represents a second angle between the horizontal direction parallel to the surface of the substrate and the light direction reflected from the substrate.

29. The optical inspection method according to claim 9, wherein the light non-refracting portions are formed from a sidewall of the lens module to a bottom surface of the lens module penetrating the lens module.

30. The lens unit according to claim 20,
wherein $\beta$ is greater than the difference of $\pi/2$ minus $\theta$,
where $\theta$ represents a first angle between a central vertical axis of the lens module and the light direction reflected from the substrate, and
$\beta$ represents a second angle between the horizontal direction parallel to the surface of the substrate and the light direction reflected from the substrate.

31. The lens unit according to claim 20, wherein the first and second light non-refracting portions are formed from a sidewall of the lens module to a bottom surface of the lens module penetrating the lens module.

* * * * *